United States Patent
Samman et al.

(10) Patent No.: US 6,474,139 B2
(45) Date of Patent: Nov. 5, 2002

(54) COMBUSTIBLE GAS DIODE SENSOR

(75) Inventors: Amer Mohammad Khaled Samman, Dearborn, MI (US); Samuel Admassu Gebremariam, Detroit, MI (US); Lajos Rimai, Ann Arbor, MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 10/068,520

(22) Filed: Feb. 6, 2002

(65) Prior Publication Data

US 2002/0092342 A1 Jul. 18, 2002

Related U.S. Application Data

(62) Division of application No. 09/891,643, filed on Jun. 25, 2001, now Pat. No. 6,378,355, which is a division of application No. 09/026,776, filed on Feb. 20, 1998, now Pat. No. 6,298,710.

(51) Int. Cl.[7] .............................................. G01N 27/00
(52) U.S. Cl. ..................... 73/31.06; 73/23.31; 422/94
(58) Field of Search ........................... 73/23.31, 31.05, 73/31.06; 422/88, 94

(56) References Cited

U.S. PATENT DOCUMENTS

| | | | |
|---|---|---|---|
| 4,450,428 A | 5/1984 | Ohta et al. | |
| 4,892,834 A | * 1/1990 | Rauh | 436/149 |
| 4,928,513 A | 5/1990 | Sugihara et al. | |
| 4,947,104 A | * 8/1990 | Pyke | 324/71.5 |
| 4,984,446 A | 1/1991 | Yagawara et al. | |
| 5,231,359 A | * 7/1993 | Masuda et al. | 324/675 |
| 5,417,821 A | 5/1995 | Pyke | 204/412 |
| 5,523,589 A | 6/1996 | Edmond et al. | |
| 5,591,321 A | 1/1997 | Pyke | 204/412 |
| 5,698,771 A | 12/1997 | Shields et al. | 73/31.05 |
| 5,942,674 A | 8/1999 | Logothetis et al. | |
| 6,027,954 A | 2/2000 | Hunter | 438/49 |
| 2001/0032493 A1 | 10/2001 | Samman et al. | 73/31.06 |

FOREIGN PATENT DOCUMENTS

| | | | |
|---|---|---|---|
| JP | 63-071647 | 4/1988 | 73/31.06 |
| WO | WO09534 | 3/1996 | 73/31.06 |

OTHER PUBLICATIONS

"Epitaxial growth of AlN by plasma–assisted, gas–source molecular beam epitaxy", by L. B. Rowland et al, J. Mater. Res. vol. 8, No. 9, Sep. 1993, pp. 2310–2314.

"Epitaxial growth of cubic AlN films on (100) and (111) silicon by pulsed laser ablation", by Wen–Tai Lin et al, Appln. Phys. Lett. 66(16), Apr. 17, 1995, pp. 2066–2068.

"Gas sensitive field effect devices for high temperatures", by A. Baranzahi et al, Sensors & Actuators B 26–27, 1995, pp. 165–169.

"Epitaxial growth of AlN thin films on silicon (111) substrates by pulsed laser deposition", by R.D. Vespute et al, J. Appl. Phys. 77 (9), May 1, 1995, pp. 4724–4728.

"High quality AlN and GaN epilayers grown on (00.1) sapphire, (100), and (111) silicon substrates", by P. Kung et al, Appl. Phys. Lett. 55 (22), May 29, 1995, pp. 2958–2960.

"Fast Chemical Sensing with Metal–Insulator Silicon Carbide Structures", by Peter Tobias et al, IEEE Electron Device Letters, vol. 18, No. 6, Jun. 1977, pp. 287–289.

"Improved AlN/SiC Device Structures and Ohmic Contact Process", IBM Technical Disclosure Bulletin, vol. 38, No. 09, Sep. 1995, pp. 415–419.

* cited by examiner

Primary Examiner—Daniel S. Larkin
(74) Attorney, Agent, or Firm—Damian Porcari (57) ABSTRACT

A combustible gas sensor diode including a SiC semiconductor substrate, on top of which an AlN layer and a catalytic metal "gate" electrode are deposited is disclosed. The combustible gas sensor diode can be operated in either a D.C. forward conduction mode or an A.C. reverse bias mode. Methods of detecting combustibles in both D.C. and A.C. modes are further disclosed.

1 Claim, 7 Drawing Sheets

COMBUSTIBLE GAS DIODE SENSOR

This is a divisional of application Ser. No. 09/891,643, filed on Jun. 25, 2001, now U.S. Pat. No. 6,378,355, issued Apr. 30, 2002, entitled COMBUSTIBLE GAS DIODE SENSOR, which is a divisional of prior application Ser. No. 09/026,776, filed Feb. 20, 1998, now U.S. Pat. No. 6,298,710, issued Oct. 9, 2001, entitled COMBUSTIBLE GAS DIODE SENSOR.

FIELD OF THE INVENTION

This invention relates to a combustible gas diode sensor including a SiC semiconductor substrate on top of which an AlN layer and a catalytic metal "gate" electrode are deposited. The resulting devices can be operated in either a D.C. forward conduction or an A.C. reverse bias mode.

BACKGROUND

MOS combustible gas sensors operate by catalytic oxidation of combustible gases at the "gate". Substantial efforts have been expended in recent years towards the development of combustible gas sensors using semiconductor MOS technology.

Generally the MOS gas sensor consists of a semiconductor substrate with an ohmic contact on one side and with the other side covered by a $SiO_2$ insulating layer with a metal gate on top. The metal gate is composed of a metal capable of catalyzing the oxidation of combustible gases. As a result of catalytic redox reactions on the gate surface, certain atomic and molecular species are generated which can diffuse through the porous gate to the metal gate/insulator interface where they can ionize. These ions can penetrate through the insulator thereby changing the potential distribution across the device. This changes the potential of the insulator/semiconductor interface and thus the depletion layer inside the semiconductor which in turn shifts the voltage dependent A.C. admittance characteristic of the device along the voltage axis.

In order to be sensitive to combustibles other then $H_2$, the catalytic gate and, therefore, the device have to be operated at temperatures above 400° C., requiring the use of a wide band gap semiconductor such as SiC instead of Si. However, at such high temperatures the $SiO_2$ layer becomes less insulating as the ionic charges within the layer become mobile. Under these conditions the device acts as a true capacitor only when biased in depletion (e.g., for n-type SiC, the gate voltage is negative with regard to the back contact). In accumulation, it begins showing some D.C. conduction. However, as the conduction process in the $SiO_2$ is different from that in the SiC, there will be a finite voltage (the barrier potential) at which there is onset of this forward conduction. This barrier potential will depend on the charges injected into the $SiO_2$ insulator by the chemical processes at the gate. As changes in this barrier voltage are directly reflected as changes in the current/voltage D.C. characteristic in the forward direction, a sensor response can be obtained by measuring changes in this characteristic as a function of changes in the combustible concentration near the catalytic gate. However, the mobility of charges in $SiO_2$ is still relatively low. Therefore, to obtain a reasonable forward current with reasonable applied voltage the thickness of this $SiO_2$ layer has to be very small, leading to breakdown instabilities.

SUMMARY OF THE INVENTION

The present invention provides a combustible gas sensor consisting of a diode structure which includes a silicon carbide semiconductor substrate having a metal back contact juxtaposed thereto. An AlN layer is deposited onto the SiC semiconductor substrate and a thin porous catalytically active metal electrode "gate" is deposited on the AlN layer.

This diode structure allows the detection of combustibles, such as hydrocarbons and carbon monoxide in a gas flow in a wide concentration range with the adjustment of certain parameters, such as the oxygen concentration. This device is compatible with semiconductor electronic technology and is substantially more robust than devices requiring membrane support for low thermal mass as the micro-calorimeter. The device further can be operated in either a forward conduction D.C. or a reverse bias A.C. response mode, the former not requiring radio frequency techniques.

In the D.C. mode embodiment, there is provided a method of detecting combustibles in a gas stream by placing a forward biased diode sensor in contact with the gas stream, wherein the diode sensor comprises a silicon carbide semiconductor substrate; a metal back contact juxtaposed to the silicon carbide semiconductor substrate; an AlN layer deposited onto the silicon carbide semiconductor substrate; and a catalytically active metal "gate" electrode deposited on the AlN layer. The method further includes the step of applying a constant forward current to the diode sensor and measuring changes in the forward voltage drop across the diode sensor as the response to changes of the combustible concentration in the gas stream. Alternatively, a constant forward bias may be applied across the sensor measuring changes in the forward current through the device as the response to changes of the combustible concentration in the gas stream.

In the A.C. mode, the present invention also provides a method of detecting combustibles in a gas stream, by placing the reverse biased diode sensor in contact with the gas stream, wherein the diode sensor comprises a silicon carbide semiconductor substrate; a metal back contact in mating engagement with the silicon carbide semiconductor substrate; an AlN layer deposited onto the SiC semiconductor substrate; and a catalytically active metal gate deposited on the AlN layer. The method next involves the step of measuring the capacitance of the diode sensor at frequencies between 10 and 3000 KHz. A constant reverse bias voltage is applied across the diode sensor. Lastly, the method requires the step of detecting a change in the capacitance in response to a change of the combustible concentration in the gas stream.

BRIEF DESCRIPTION OF THE DRAWINGS

FIG. 5 is a graph illustrating the D.C. real time response of a Pt/AlN/SiC sensor diode to CO in the absence of $O_2$.

The ordinate for the CO concentration is indicated by the right vertical axis. The total flow is in 1000 sccm $N_2$;

DESCRIPTION OF THE PREFERRED EMBODIMENT(S)

Figure 1:
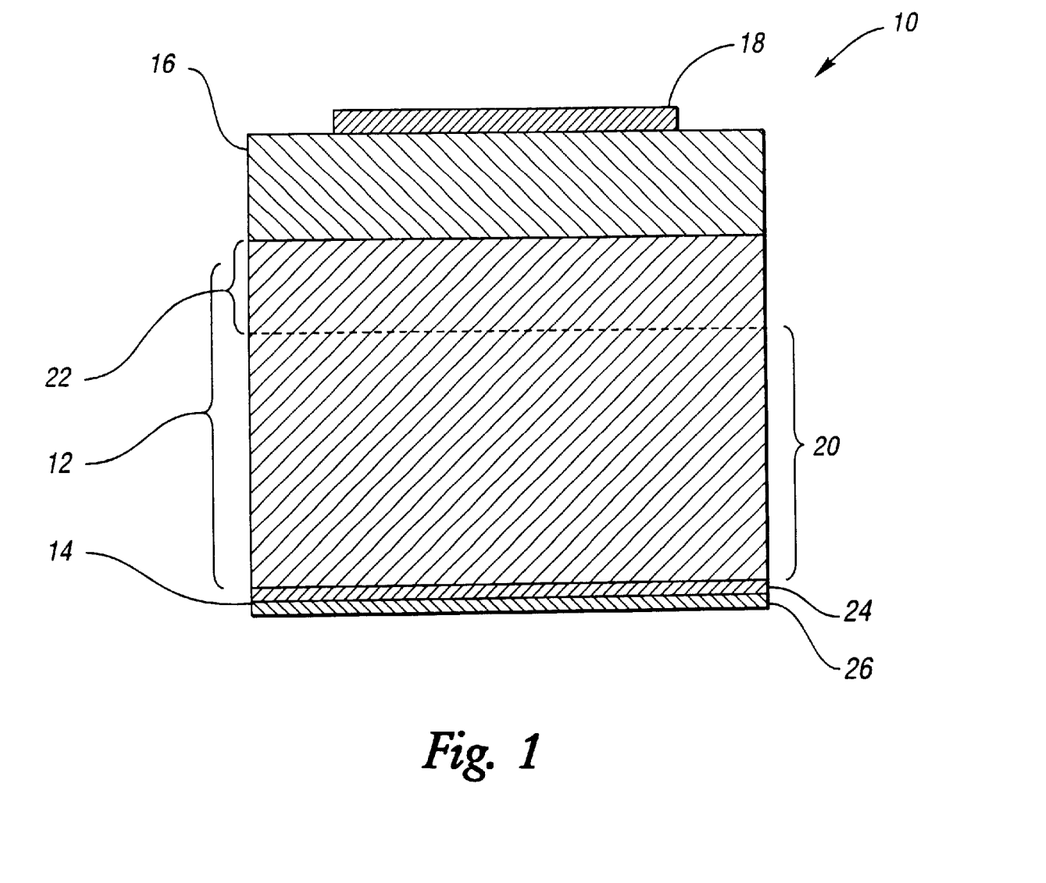
FIG. 1 illustrates a simple diagram of a gas sensor diode structure.

A simple model of the gas sensor structure 10 is shown schematically in FIG. 1. The sensor structure 10 includes a semiconductor 12, a metal back contact 14, an AlN layer 16, and a catalytic metal "gate" electrode 18. For high temperature applications, the preferred semiconductor is SiC, due to its ability to operate at temperatures well in excess of 400° C. necessary for achieving catalytic oxidation-reduction of hydrocarbons as well as CO. The metal back contact 14 is preferably made of tantalum, titanium, nickel or their silicides with an outside layer of Pt to prevent high temperature oxidation. Laser ablated Pt film on SiC by itself will also make an acceptable ohmic metal back contact at such high temperatures.

The structure of the present invention can be used as a sensor in two different modes depending on the range of the gate bias: (1) in a D.C. mode by measuring the voltage across the device needed to maintain a constant forward current, or by measuring the current through the device when a constant forward voltage is applied across it; and (2) using the small signal A.C. measurement of the device capacitance when a reverse voltage is applies across it.

Under the present invention, and as depicted in FIG. 1, a diode structure is disclosed which includes a metal gate 18 over an AlN layer 16 grown over a SiC semiconductor substrate 12 with a metal back contact 14. The 2H-AlN layer is deposited by laser ablation of a stoichiometric AlN target, onto a SiC carbide 6H wafer 20 with a 10 $\mu$m n-type homoepilayer 22, nitrogen doped with a $10^{16} cm^{31\ 3}$ nominal donor concentration. This substrate was cut at vicinal (0001) orientation (3.50 inclination) and is a standard commercially available item. The AlN deposition was carried out in a vacuum chamber at a base pressure of $5 \times 10^{-7}$ torr, onto the heated substrate held at 900 C. The 351 nm radiation from the XeF excimer was used at fluences in the range of 1.5 to 3 $J/cm^2$. At room temperature the AlN films were insulating. For the large majority of films on SiC, the θ-2θ x-ray diffraction scans were strongly dominated by the 0006 SiC and 0002 AlN reflections. The ohmic back contact consisted of a tantalum layer 24 covered by a platinum film 26 deposited sequentially by laser ablation of the respective targets. Laser ablation was also used to deposit the metal gate electrodes 18, preferably platinum, on top of the AlN layer 16. In the preferred embodiment, the metal gate electrode consists of platinum having a thickness in the range of 1000–2000 angstroms deposited onto the AlN layer having a thickness between 1700–2000 angstroms. The metal back contact consists of a 500 angstrom tantalum layer with a 1000–2000 angstroms platinum layer deposited thereon.

Figure 2:
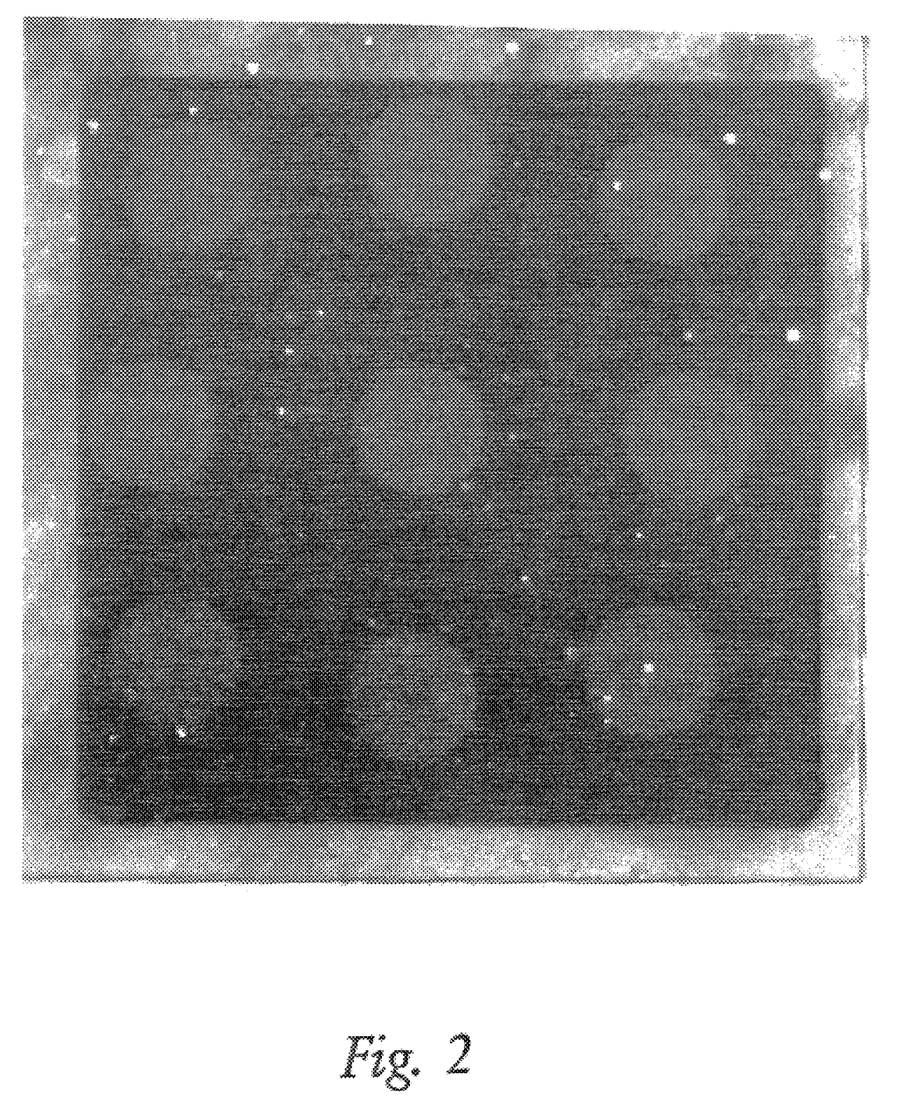
FIG. 2 is a plane view optical microphotograph of a set of nine Pt/AlN/SiC sensor diodes fabricated on a common substrate. The circular patches are the 1 mm diameter Pt gates.

FIG. 2 shows an optical microphotograph of a set of typical sensor devices.

Figure 3:
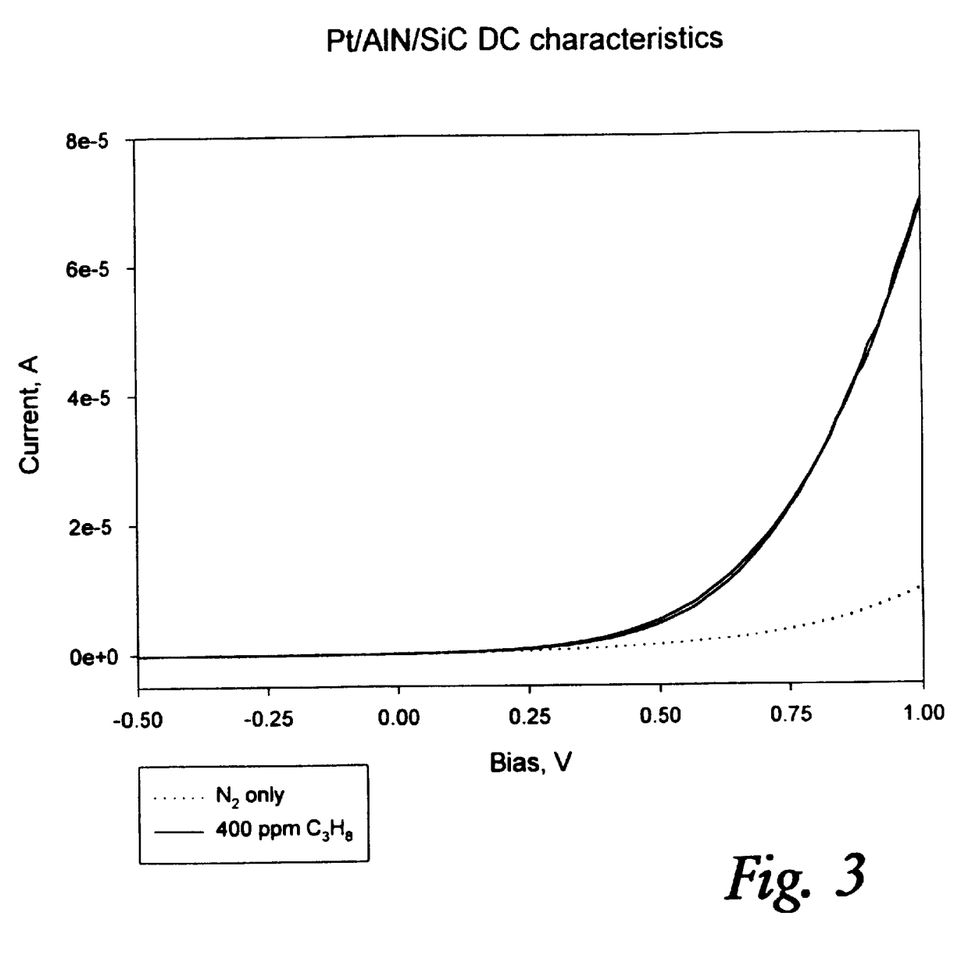
FIG. 3 is a graph illustrating the D.C. current-voltage characteristic I(V) of a Pt/AlN/SiC sensor diode at 520° C. with and without propane in the ambient gas (nitrogen). Positive voltage corresponds to the gate positively biased with respect to the back contact.

A study of the D.C. current versus voltage (I(V)) profiles of a number of these AlN gas sensor diodes demonstrate rectifying characteristics, as exemplified in FIG. 3, where the dependence of the high temperature forward I(V) profile on the presence of combustibles is clearly shown.

Hydrocarbon sensitivity of the I(V) profile has been demonstrated for SiC MOS structures with extremely thin oxide layers, thicknesses in the order of 20 to 50 angstroms, where the forward current can be explained either by tunneling through such a narrow potential barrier, or by direct thermal emission in the Schottky diodes that might have formed directly between the SiC and the gate in regions of discontinuity of such a thin $SiO_2$ film. In the present case, the AlN layer has a thickness between 1700 and 2000 angstroms making current conduction by such mechanisms unlikely. AlN is actually a wide band gap semiconductor, with an energy gap in the vicinity of 6 eV. This would make the device structure that of a heterojunction with metal/semiconductor contacts on both outside surfaces. Such structures generally will have rectifying I(V) characteristics. AlN being a semi-conductor with electrons as charge carriers exhibits a greater mobility and is thus a suitable material to replace the much thinner $SiO_2$ layer used in prior diode devices. It is conceivable that in the present structures, charge carriers in the AlN are provided by doping with donors or acceptors, either due to a small deviation from stoichiometry, or due to inclusion of impurities such as Si or C from the substrate. A voltage barrier will still exist at the AlN-SiC interface as the band gaps of the two materials are widely different, and this voltage barrier will still be affected by any charges injected at the gate, as such charges will affect the distribution of electrons in the AlN. Thus, such heterojunction diodes will behave as combustible sensors when used in the forward bias D.C. mode.

These devices can also be used in the reverse bias A.C. mode as capacitive combustible sensors. The tantalum/platinum contact on the back of the SiC substrate can be considered as ohmic.

Figure 4:
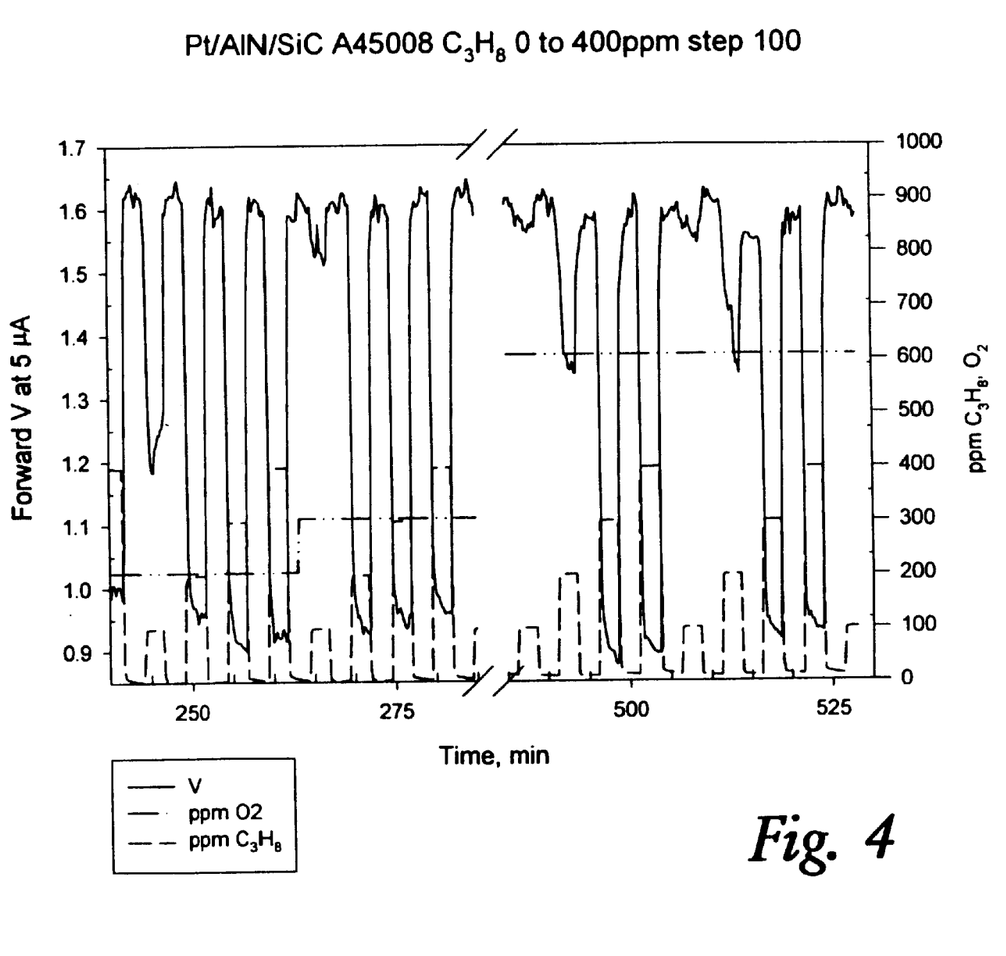
FIG. 4 is a graph illustrating the D.C. real time response of a Pt/AlN/SiC sensor diode to propane in a background concentration of $O_2$ in 1000 sccm $N_2$. The propane and oxygen concentrations are indicated by the right vertical axis.
Figure 5:
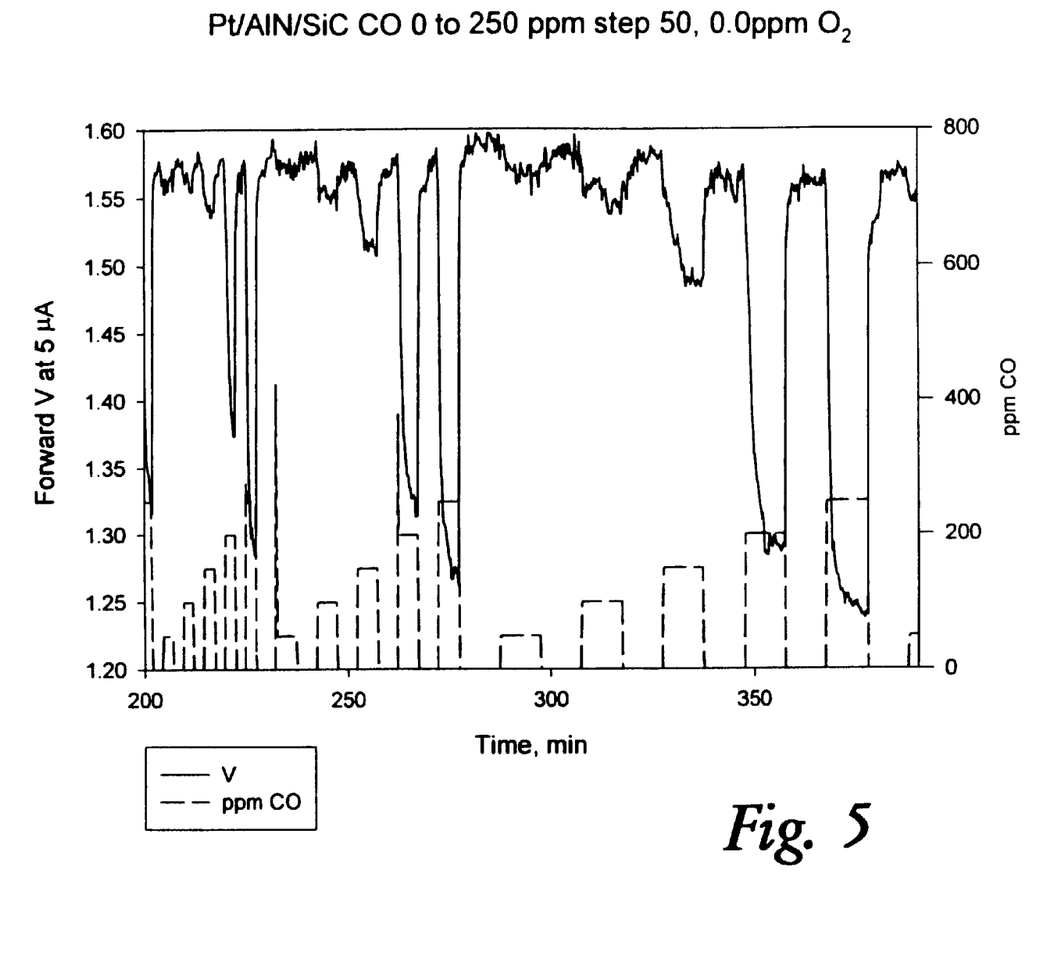

FIGS. 4 and 5 illustrate the real time D.C. response of an AlN gas sensor to time dependent combustible concentration changes in the surrounding flow. The output on the ordinate axis corresponds to the voltage across the device for a forward current of 5 $\mu$A maintained through the device (with the gate biased positively with respect to the back contact). The combustibles are propane in FIG. 4 and CO in FIG. 5. The data for propane shows that there is saturation under very rich conditions, but that the device sensitivity can be adjusted by varying the oxygen concentration. Such effects were also recorded for CO, and propylene. By maintaining the oxygen concentration in an appropriate range, sensitivity to a few ppm per carbon atom can be realized.

Figure 6:
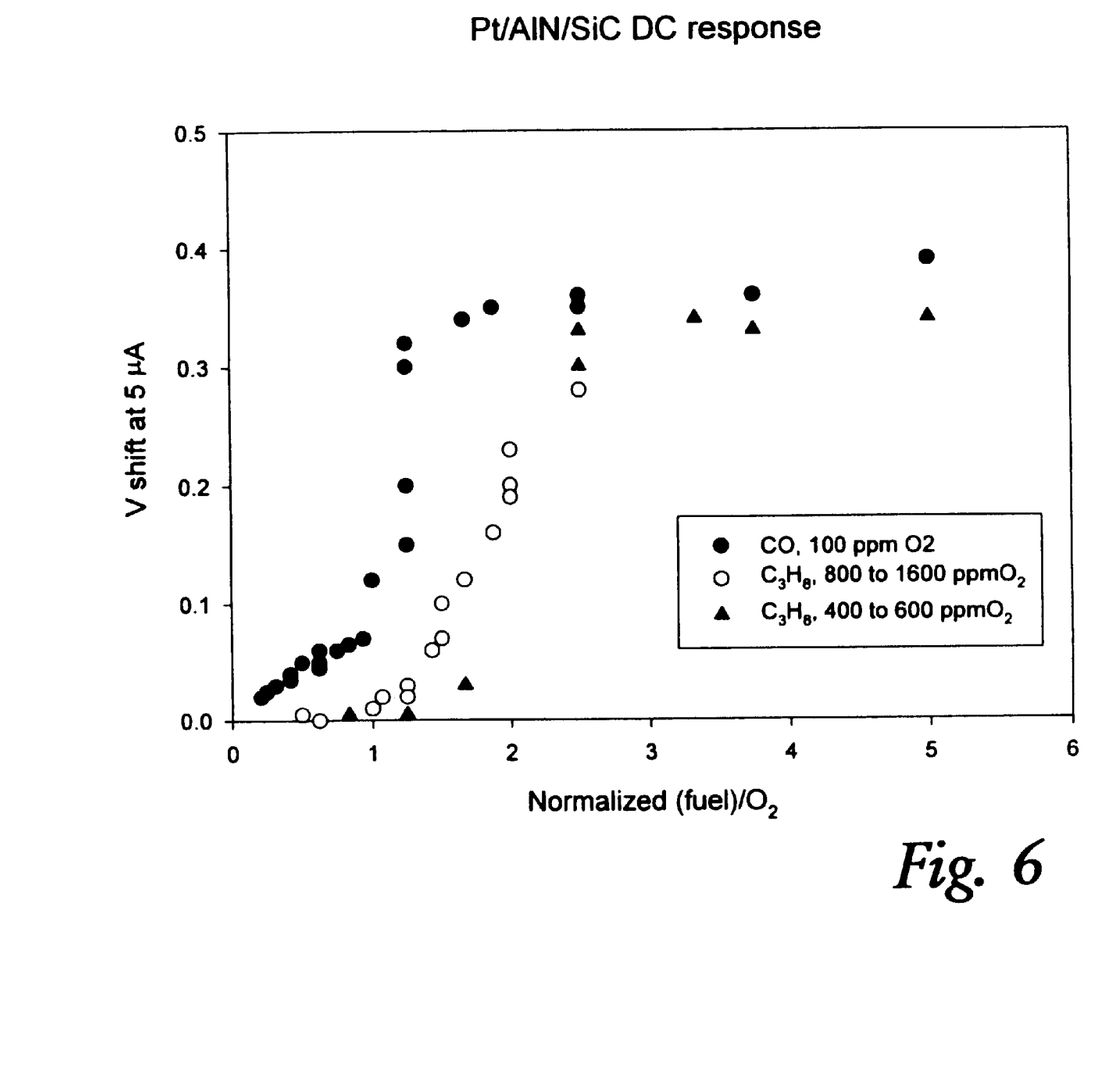
FIG. 6 is a graph illustrating the D.C. responses of a Pt/AlN/SiC sensor diode to propane and CO plotted as a function of the combustible to oxygen ratio normalized to exact stoichiometry for a wide range of oxygen concentrations. The response is measured by the shift in the forward voltage (at a forward current of 5 $\mu$A) across the device.

FIG. 6 summarizes the responses obtained for CO and propane, in terms of the absolute value of the shift of the voltage across the device from its value for zero hydrocarbon concentration (ordinate). The abscissa is the relative combustible to oxygen ratio, normalized to its value at exact stoichiometry. Clearly the sensitivity is not solely a function of this fuel/oxidizer ratio, but also depends on the specific combustible. This is related to the fact that the flow gas composition is being sensed via some molecular or atomic species present in the reacting mixture in the vicinity of the catalytic gate, and which is not in thermal equilibrium with the main gas flow. This circumstance, albeit a complicating factor, endows these devices with the potential for use as selective combustible sensors.

Figure 7:
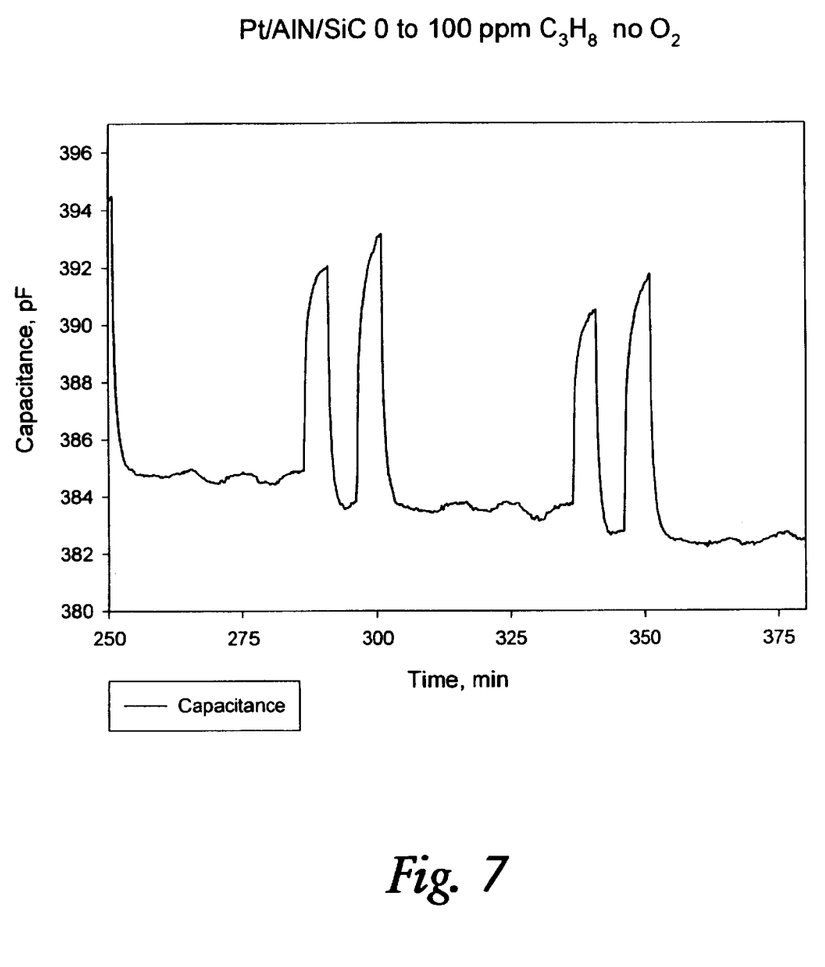
FIG. 7 is a graph illustrating the real time reverse bias capacitance response at 1 MHz of a Pt/AlN/SiC sensor diode to a sequence of rectangular 5 min duty cycle pulses of CO 0 to 100 ppm in amplitude and increasing in steps of 20 ppm.

FIG. 7 illustrates the real time capacitance change of a reverse bias AlN device in response to CO concentration changes. CO concentration was varied in rectangular pulses of increasing amplitudes between 0 and 100 ppm.

While the present invention has been described in detail in connection with the above examples, it is to be understood that such detail is solely for that purpose and that variations can be made by those skilled in the art without departing from the spirit of the invention.

What is claimed is:

1. A method of detecting combustibles in a gas stream, comprising:

placing a reverse biased diode sensor in contact with the gas stream, wherein the diode sensor comprises:

a SiC semiconductor substrate;

a metal back contact juxtaposed to the SiC semiconductor substrate;

an AlN layer deposited on the SiC semiconductor substrate; and a catalytically active metal gate deposited on the AlN layer;

measuring the capacitance of the diode sensor at frequencies between 100 and 1000 KHz; and detecting a shift in the capacitance versus voltage characteristics of the diode sensor.

* * * * *